(12) United States Patent
Chen

(10) Patent No.: US 9,433,991 B2
(45) Date of Patent: Sep. 6, 2016

(54) APPARATUS AND METHOD FOR STENT SHAPING

(71) Applicant: Edwards Lifesciences Corporation, Irvine, CA (US)

(72) Inventor: Harvey H. Chen, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 968 days.

(21) Appl. No.: 13/675,678

(22) Filed: Nov. 13, 2012

(65) Prior Publication Data

US 2013/0160512 A1 Jun. 27, 2013

Related U.S. Application Data

(60) Provisional application No. 61/578,764, filed on Dec. 21, 2011.

(51) Int. Cl.
*B21D 26/033* (2011.01)
*A61F 2/90* (2013.01)
*B21D 26/041* (2011.01)

(52) U.S. Cl.
CPC ............. *B21D 26/033* (2013.01); *A61F 2/90* (2013.01); *A61F 2230/005* (2013.01); *A61F 2230/0067* (2013.01); *A61F 2230/0076* (2013.01); *A61F 2230/0078* (2013.01); *A61F 2240/001* (2013.01); *A61F 2250/0039* (2013.01); *B21D 26/041* (2013.01)

(58) Field of Classification Search
CPC B21D 26/033; B21D 26/029; B21D 26/045; B21D 26/021; B21D 26/041; B21D 21/047

USPC ......................................... 72/63, 370.22, 402
See application file for complete search history.

(56) References Cited

U.S. PATENT DOCUMENTS

| 4,352,280 | A | * | 10/1982 | Ghosh ................. B21D 26/021 72/364 |
|---|---|---|---|---|
| 5,085,068 | A | * | 2/1992 | Rhoades .............. B21D 26/021 72/54 |
| 5,626,604 | A | | 5/1997 | Cottone, Jr. |
| 5,630,830 | A | | 5/1997 | Verbeek |
| 5,810,838 | A | | 9/1998 | Solar |
| 6,682,546 | B2 | | 1/2004 | Amplatz |
| 2003/0116260 | A1 | | 6/2003 | Chobotov et al. |
| 2006/0155367 | A1 | | 7/2006 | Hines |
| 2007/0038290 | A1 | | 2/2007 | Huang et al. |
| 2008/0254159 | A1 | | 10/2008 | Brown et al. |
| 2011/0307070 | A1 | | 12/2011 | Clerc et al. |

FOREIGN PATENT DOCUMENTS

WO 2005025453 A2 3/2005

* cited by examiner

*Primary Examiner* — Alexander P Taousakis
*Assistant Examiner* — Pradeep C Battula
(74) *Attorney, Agent, or Firm* — AnneMarie Kaiser; Guy Cumberbatch; Pui Tong Ho

(57) ABSTRACT

An apparatus for crimping a radially expandable stent includes a pressure vessel, shaping balloon, and mandrel. The mandrel is configured to slidingly receive a stent thereon, and to be slidingly advanced into the pressure vessel. The shaping balloon is inflated to radially compress the stent onto the form of the mandrel; such compression need not be uniform. Pressurization of the shaping balloon facilitates the expansion of the balloon to achieve compression of the stent, with depressurization of the shaping balloon causing the balloon to return to an unexpanded state.

22 Claims, 5 Drawing Sheets

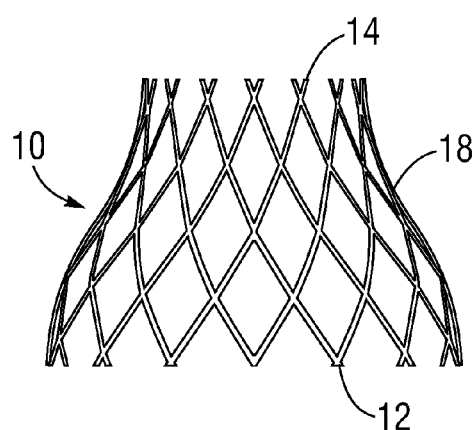
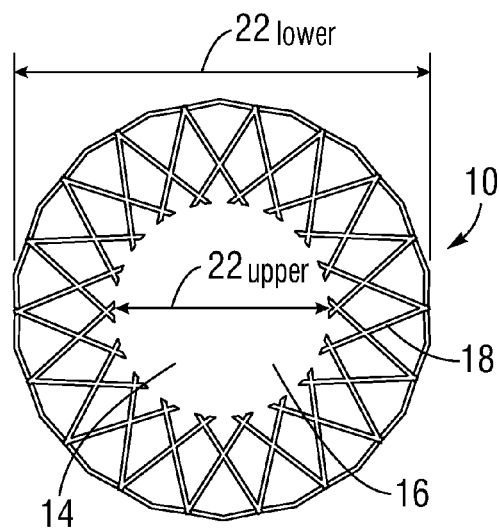
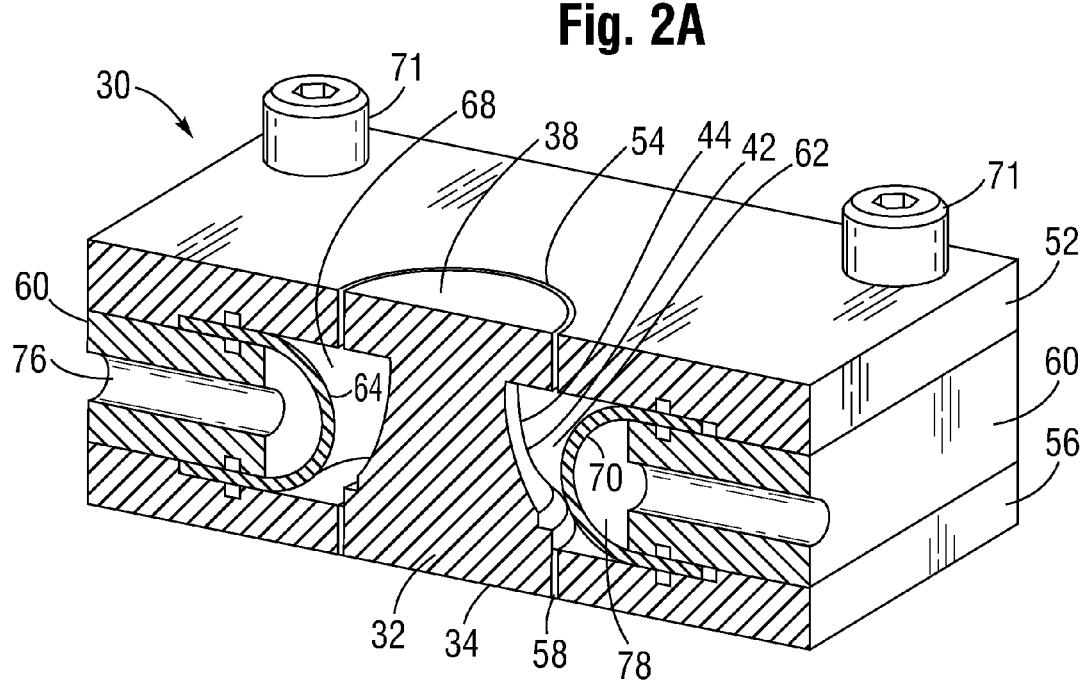

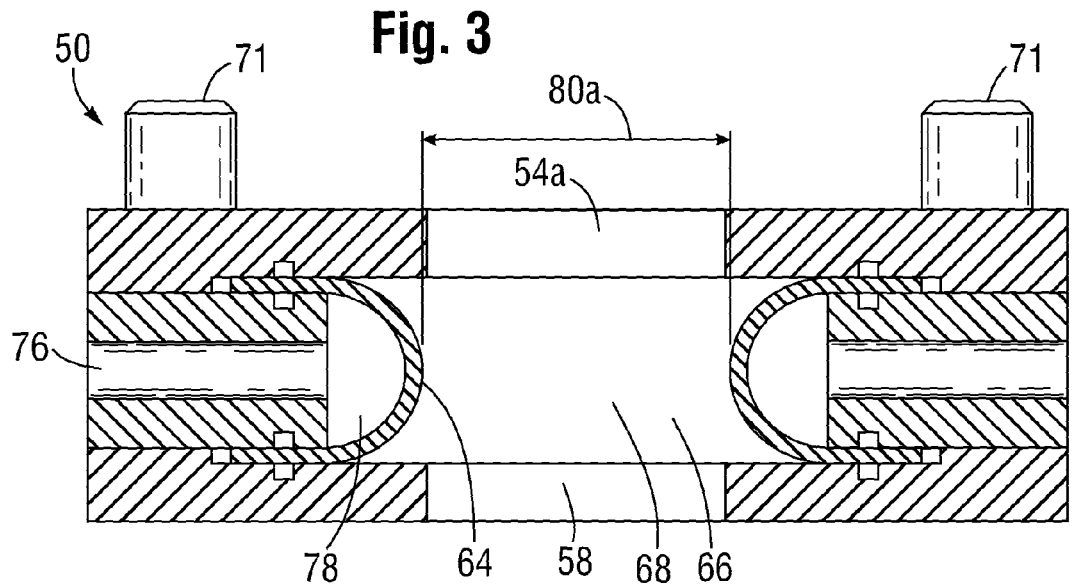
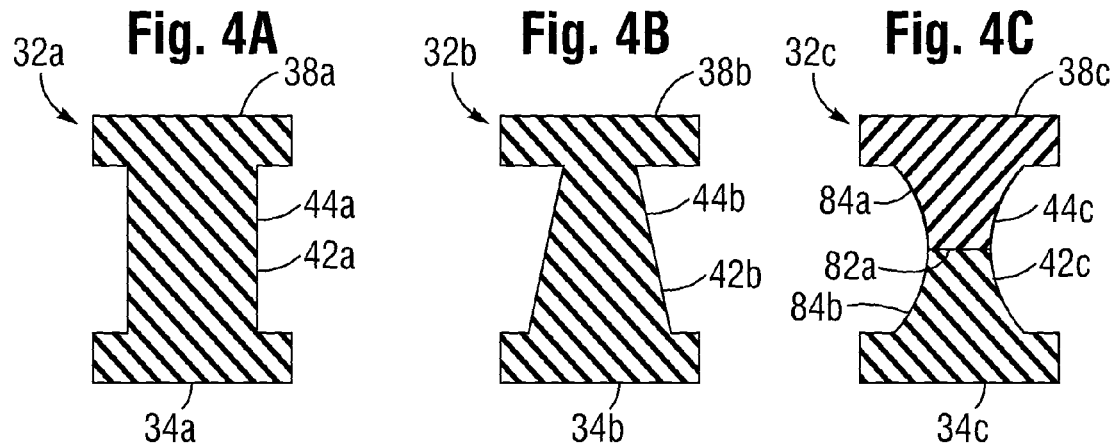
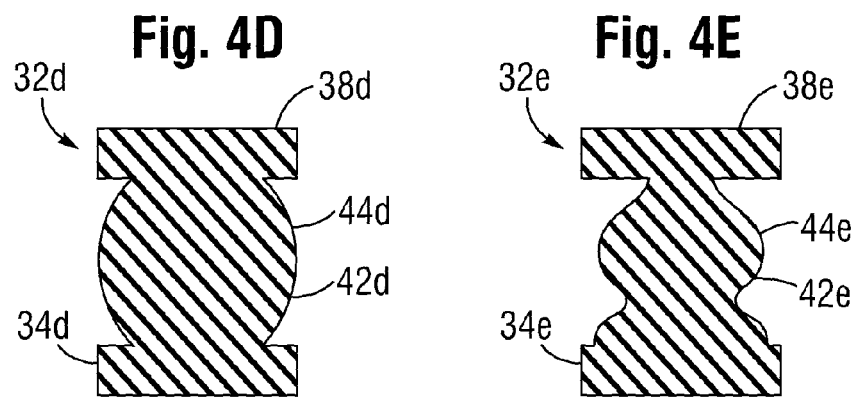

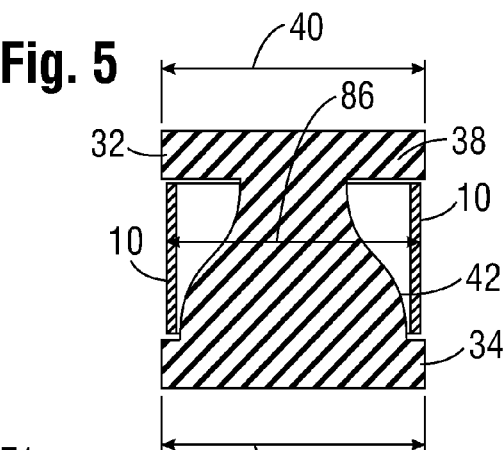
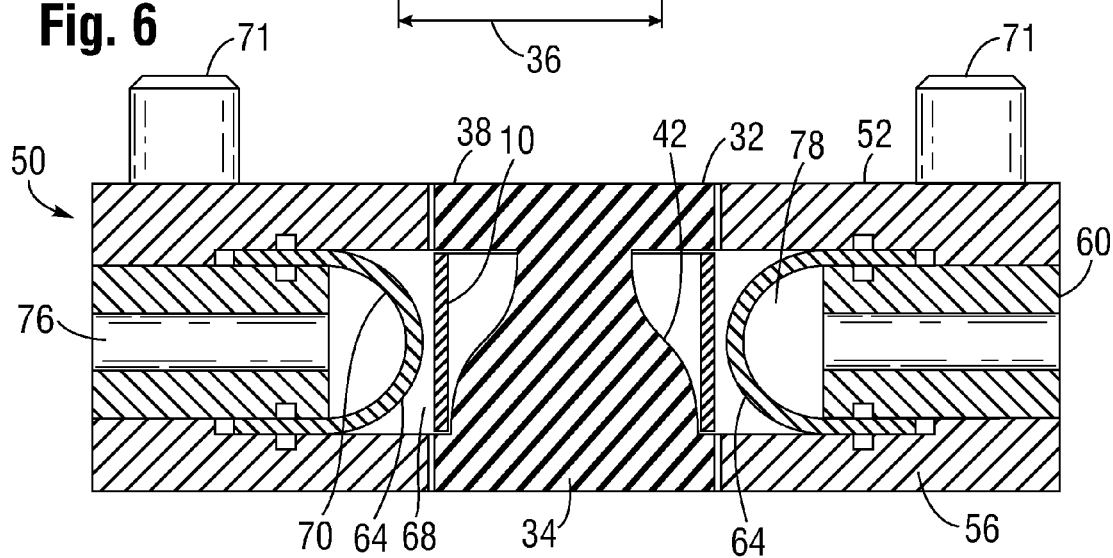
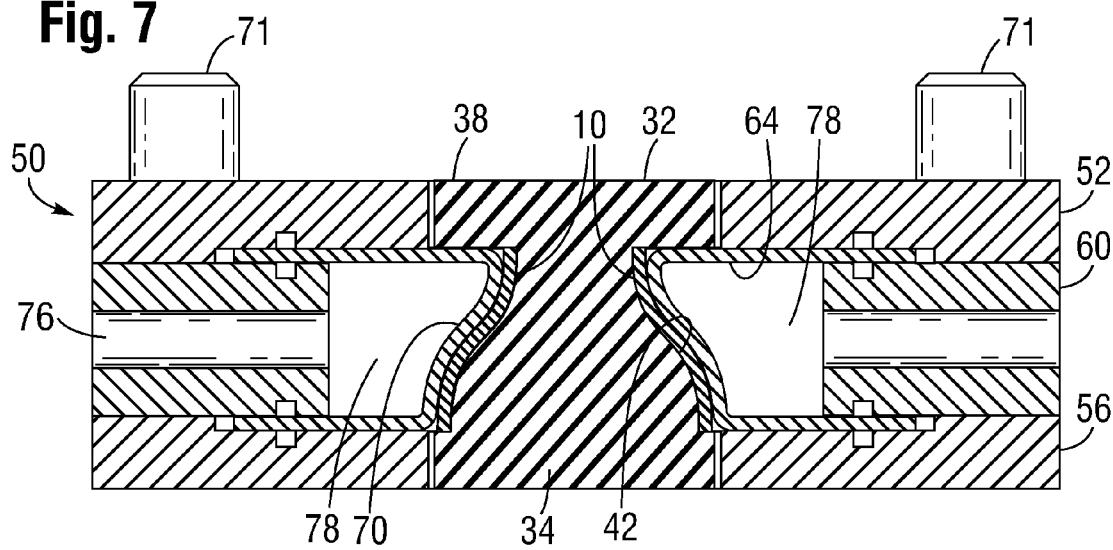

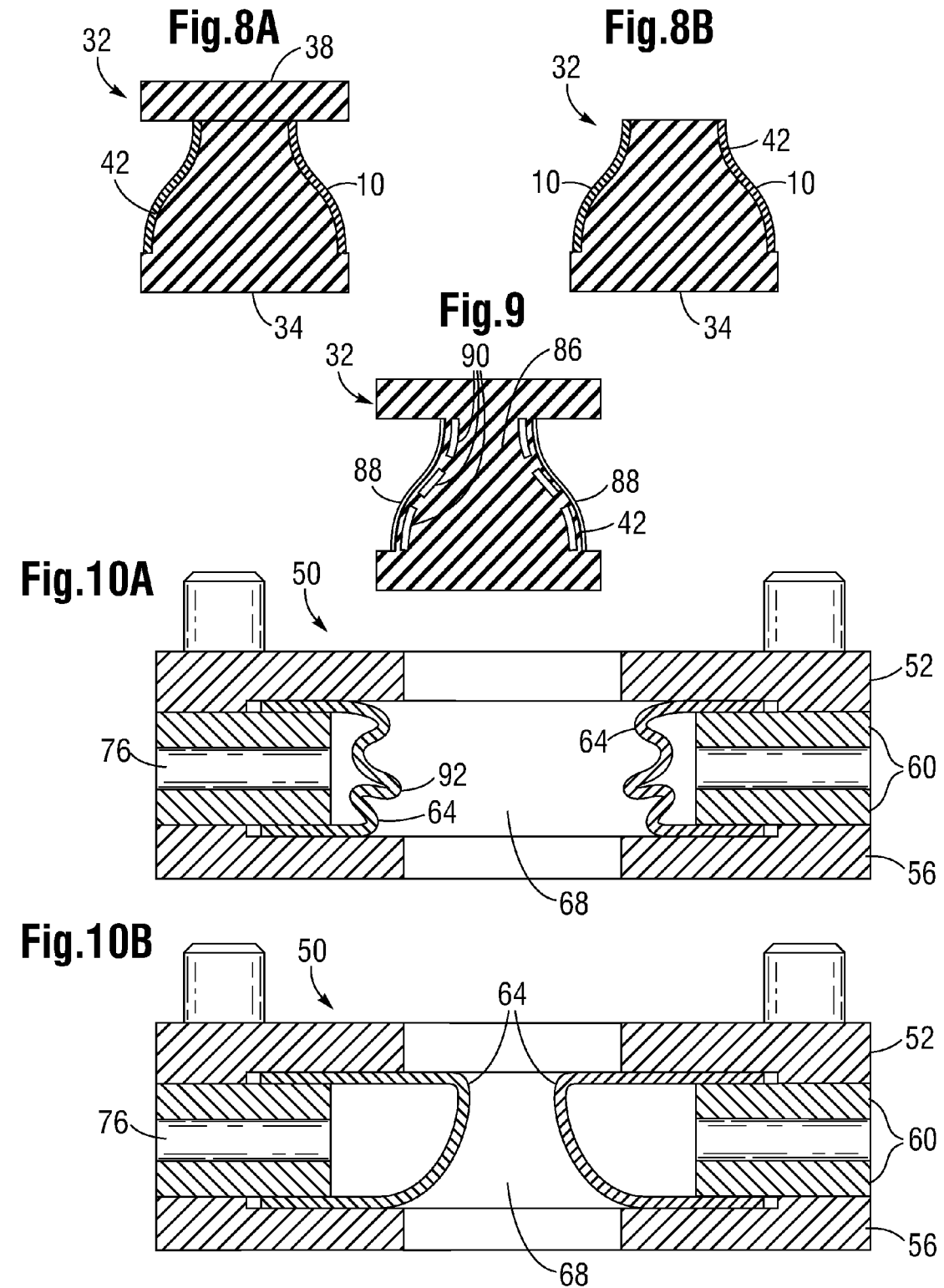

APPARATUS AND METHOD FOR STENT SHAPING

RELATED APPLICATION

This application claims priority under 35 U.S.C. §119(e) to U.S. Provisional Application No. 61/578,764, filed Dec. 21, 2011, the entire disclosure of which is hereby incorporated by reference.

FIELD OF THE INVENTION

The present invention relates to methods and apparatus used to shape stents, particularly those used for medical devices. More specifically, the present invention relates to methods and apparatus for pneumatically and/or hydraulically shaping stents and similar structures, including devices having stents for support.

BACKGROUND OF THE INVENTION

The term "stent" is generally used to refer to medical devices and/or supports therefore which can be implanted in anatomical passageways (e.g., blood vessels, valve annuluses, body ducts, etc.) of the body for the purpose of maintaining the patency or state of dilation of the passageway, reinforcing the passageway, or anchoring a valve or graft or other object within the passageway. For purposes of this application, the term "stent" is used to refer to such supports, including supports intended for radial expansion as well as supports which are not intended for radial expansion.

Many stents are not intended for delivery and subsequent expansion via catheter, but are instead delivered and deployed in their full form and shape. Examples of such stents include supports for surgical heart valves and grafts. Stents for delivery via catheterization may be initially disposed in a compact configuration of relatively small diameter upon or within a delivery catheter to facilitate insertion and advancement of the stent into a desired anatomical passageway. Once at the implantation site, such stents may be radially expanded to a larger diameter which is equal to or slightly larger than the diameter of the anatomical passageway in which the stent is to be implanted. When radially expanded to the larger diameter, the stent may be released from the delivery catheter, and left in place where it is anchored (e.g., via frictional engagement) to the surrounding wall of the anatomical passageway.

In general, expandable stents fall into two major categories: a) self-expanding and b) balloon-expandable. Self-expanding stents may be formed of resilient or shape memory material (e.g., spring steel or nitinol) which is capable of self-expanding from a relatively small delivery diameter to a larger deployed diameter, with the expansion being achieved by releasing the stent from its compressed configuration whereupon it expands to its larger diameter in spring-like fashion. Balloon-expandable stents may be formed of plastically deformable material (e.g., stainless steel) which can be radially expanded by inflating a balloon positioned within inner lumen of the stent.

Stents can be provided in various sizes and shapes. Many stents are simple cylindrical forms and have substantially constant diameters along their lengths. However, for some applications it may be desirable for a stent having a more complex shape, including shapes where the diameter of the stent varies substantially along the length of the stent.

Stent shapes can be defined using various techniques. One common device for shaping stents is a crimper. Current stent crimpers tend to be purely mechanized devices that crimp stent frames into basic geometric shapes such as constant-diameter cylinders and simple cones. They have relatively complex mechanisms but are limited to forming relatively simple shapes.

What are needed are crimping devices and methods for forming stents in complex shapes using a relatively simple forming mechanism. The current invention meets these needs.

SUMMARY OF THE INVENTION

An apparatus for shaping stents includes a pressure vessel and mandrel. The pressure vessel has an upper plate with an upper plate opening, a lower plate with a lower plate opening, and a central plate assembly with a central plate and central plate opening. The central plate assembly includes a shaping balloon defining a balloon interior chamber, with the shaping balloon passing around the inner perimeter of the central plate opening and forming a balloon central opening in the radial center of the shaping balloon. The shaping balloon has an inflated configuration and a deflated configuration. The upper plate and lower plate and central plate are stacked together, with the central plate positioned between the upper plate and the lower plate. When the plates are thus stacked, the lower plate opening, upper plate opening, and balloon central opening form a continuous mandrel-receiving lumen.

The apparatus also includes a mandrel sized and configured to be advanced along its longitudinal axis into the mandrel-receiving lumen of the pressure vessel. The mandrel has an upper mandrel plate, a lower mandrel plate, and a central mandrel portion. The upper mandrel plate has a shape configured to fit tightly into the upper frame plate opening, and the lower mandrel plate has a shape configured to fit tightly into the lower frame plate opening. The central mandrel portion has a shape corresponding to a desired stent shape, wherein the mandrel is sized and configured to be slidingly advanced along its longitudinal axis into the mandrel-receiving lumen.

The central plate assembly may have a fluid lumen in fluid communication with the balloon interior chamber. Fluid can be provided into the fluid lumen to inflate the balloon, and the fluid can also be removed through the fluid lumen to deflate the balloon. The fluid lumen may pass radially through a portion of the central plate. The fluid lumen includes an open end which communicates with the exterior of the apparatus. The pressurization of the balloon interior chamber via the fluid lumen facilitates the uniform compression of the shaping balloon, with the depressurization of the balloon interior chamber via the fluid lumen being operational to allow the shaping balloon to return to an uncompressed/unexpanded state.

The upper mandrel portion may have an upper diameter, with the lower mandrel portion having a lower diameter. The upper diameter may be the same as, or different from, the lower diameter. The central mandrel portion defines a stent-receiving area having one or more areas of reduced radial diameter, wherein the one or more areas of reduced radial diameter are smaller in (i.e., reduced in) diameter than at least one of the upper diameter or lower diameter. The area of reduced radial diameter may be smaller in diameter than both the upper diameter and lower diameter. The stent-receiving area may have a substantially tubular shape with a substantially constant diameter along a longitudinal length thereof. The stent-receiving area may have a substantially tubular shape having varying diameters along a longitudinal length thereof. For a mandrel for use in shaping a prosthetic heart valve stent, the varying diameters may be between about 15 mm and 35 mm, with longitudinal lengths which may be about 8 mm to 40 mm. Diameters of 20 mm to 30 mm (which may be constant or varying along the length of the mandrel) are also within the scope of the invention, as are lengths of 8 mm to 10 mm.

A stent may be positioned on the stent-receiving area of the mandrel. The stent may be formed from biocompatible material, such as stainless steel or shape-memory material (e.g., nitinol), and may have a substantially open mesh-like portion. The stent-receiving portion of the mandrel may have an outer surface which is formed from substantially flexible material, which can provide padding to cushion the stent as it is compressed against the mandrel. The mandrel may have an inner shape which is formed from substantially rigid, non-deformable material. With a substantially flexible coating on the inner shape, the stent can be compressed to form the desired shape of the rigid inner shape while still having some padding provided by the outer surface. The upper and/or lower mandrel portions may be configured to be releasably attached and re-attached to the central mandrel portion.

The stent-receiving portion of the mandrel may have heating and/or cooling capabilities, which can assist in setting the shape of a shape-memory stent such as a nitinol stent. The stent-receiving portion may include one or more heating elements, such as resistive heaters, to raise the temperature to a desired temperature.

The shaping balloon may be formed of substantially flexible and elastomeric material, or can be formed of flexible but substantially non-elastic material. The shaping balloon in its expanded configuration may form a pre-defined shape wherein the balloon central opening has a substantially continuous inner diameter, or may form a pre-defined shape wherein the balloon central opening has a substantially tubular shape having varying internal diameters along a longitudinal length thereof.

The shaping balloon may have an upper edge and a lower edge, with the upper edge of the shaping balloon sandwiched between an upper surface of the central plate and a lower surface of the upper plate, and the lower edge of the shaping balloon sandwiched between a lower surface of the central plate and an upper surface of the lower plate.

Methods of shaping a stent according to embodiments of the invention may include providing a pressure vessel, with the pressure vessel having a pressure vessel lumen, the pressure vessel further having a shaping balloon positioned circumferentially about the pressure vessel lumen and defining an central inner wall portion of the pressure vessel lumen. The shaping balloon may have a balloon opening and a balloon interior chamber, with the balloon opening defining a central lumen portion of the pressure vessel lumen, the pressure vessel further having a fluid lumen in fluid communication with the balloon interior chamber. A method may further include providing a mandrel with a stent-receiving portion, with the mandrel sized and configured to be slidingly advanced into the pressure vessel lumen to a position where the stent-receiving portion is positioned within the balloon opening. The method may include positioning a stent onto the stent-receiving portion of the mandrel, slidingly advancing the mandrel into the pressure vessel lumen to a position where the stent-receiving portion is positioned within the balloon opening, inflating the shaping balloon with sufficient pressure to cause the balloon to expand to its expanded configuration, whereby the balloon compresses against the stent to compress the stent onto the stent-receiving portion of the mandrel, whereby the stent conforms to and assumes the shape of the stent-receiving portion of the mandrel, and deflating the shaping balloon. The method may further include withdrawing the mandrel from the pressure vessel lumen, and removing the stent from the mandrel.

The mandrel may have a releasable end (upper and/or lower) configured to be removed and re-attached to the stent-receiving portion, where positioning the stent onto the stent-receiving portion involves removing the releasable end, slidingly advancing the stent onto the stent-receiving portion, and re-attaching the releasable end. The stent may be formed of stainless steel, and removing the stent from the mandrel may involve removing the releasable end, slidingly removing the stent from the stent-receiving portion, and re-attaching the releasable end. The stent may be formed of a shape memory material such as nitinol, and the method may involve, after or during the step of inflating the shaping balloon with sufficient pressure to cause the shaping balloon to expand to its expanded configuration, but prior to deflating the shaping balloon, the further step of exposing the stent to a desired shape-setting temperature, followed by exposing the stent to a desired reduced temperature. Exposing the stent to the desired shape-setting temperature may include adding to the balloon interior chamber a fluid having a temperature that is at or above the desired shape-setting temperature. Exposing the stent to the lower temperature may include adding to the balloon interior chamber a fluid having a temperature that is at or below the desired shape-setting temperature.

BRIEF DESCRIPTION OF THE DRAWINGS

Features and advantages of the present invention will become appreciated as the same become better understood with reference to the specification, claims, and appended drawings wherein:

FIGS. 1A and 1B depict side and bottom views of a stent having a complex form capable of being produced using the methods and devices of embodiments of the invention;

FIGS. 2A-2E depict a perspective (cross-section), side (cross-section), top, top (with top plate removed), and bottom views of an apparatus according to an embodiment of the invention;

FIG. 3 depicts a side view (cross-sectional) of a pressure vessel according to an embodiment of the invention;

FIGS. 4A-4E depict side views (cross-sectional) of mandrels according to various embodiments of the invention;

FIG. 5 depicts a side view (cross-sectional) of a mandrel with stent positioned thereon according to an embodiment of the invention;

FIG. 6 depicts a side (cross-sectional) view of the mandrel and stent of FIG. 5 positioned within a pressure vessel with the shaping balloon deflated according to an embodiment of the invention;

FIG. 7 depicts a side (cross-sectional) view of the mandrel and stent positioned within the pressure vessel of FIG. 6 but with the shaping balloon inflated according to an embodiment of the invention;

FIGS. 8A and 8B depict side views, assembled and exploded, of a mandrel with detachable upper and lower portions;

FIG. 9 depicts a side view, in cross-section, of a mandrel having a resilient coating and a heating element according to embodiments of the invention; and FIGS. 10A and 10B depict side views, in cross-section, of a pressure vessel and shaping balloon according to an embodiment of the invention.

DETAILED DESCRIPTION OF PREFERRED EMBODIMENTS

Figure 2B:
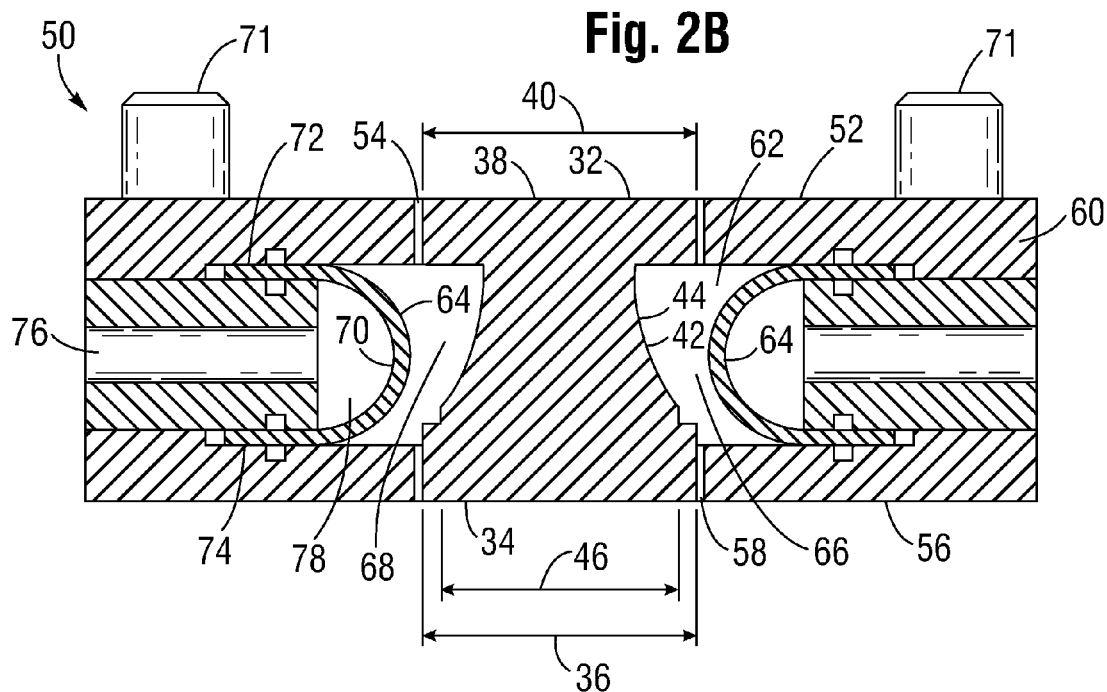

Referring now to FIGS. 1A-1B, a stent 10 is depicted having a lower opening 12, an upper opening 14, a stent lumen 16, and a main stent body 18. A mesh-like structure forms the stent wall 20. The main stent body 18 has a relatively complex form, where the inner diameter varies along the length 24 of the stent 10. At the lower opening 12, the inner diameter $22_{lower}$ is relatively large, but the inner diameter varies along the length and reaches a relatively small inner diameter $22_{upper}$ at the upper opening 14.

Figure 2C:
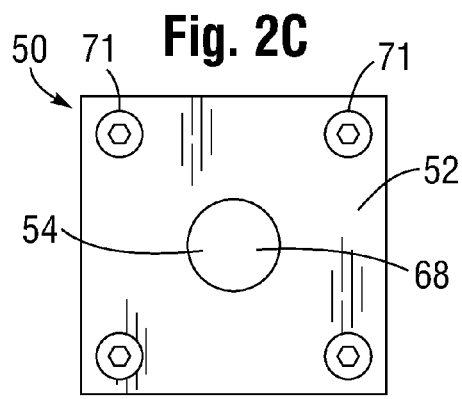
Figure 2E:
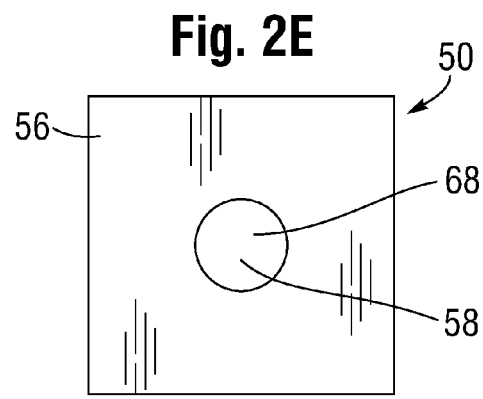
Figure 2D:
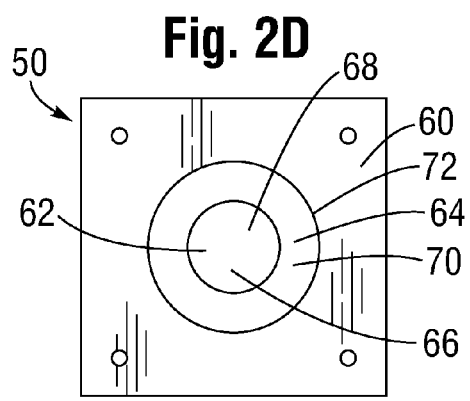

A stent shaping apparatus 30 according to an embodiment of the invention is depicted in FIGS. 2A-2E. The apparatus 30 has a mandrel 32 having a lower portion 34 with a lower diameter 36, an upper portion 38 with an upper diameter 40, and a central stent-supporting portion 42 having a varying diameter profile portion 44. The largest diameter 46 of the varying diameter profile portion 44 is less than the upper diameter 40 and also less than the lower diameter 36 so that a stent may be mounted thereon and still have, even prior to full compression, an overall outer diameter smaller than the upper diameter 38 and lower diameter 36 of the mandrel 32 in order to facilitate positioning of the mandrel and stent into the pressure vessel 50.

The pressure vessel 50 has an upper plate 52 having an upper opening 54, a lower plate 56 having a lower opening 58, and a central plate 60 having a central opening 62. A substantially ring-shaped shaping balloon 64 is positioned within the central opening 62, with an inner opening 66 defined within the shaping balloon 64. The upper opening 54, inner opening 66, and lower opening 58 are in longitudinal alignment and define a pressure vessel central lumen 68. The pressure vessel central lumen 68 is sized and configured to slidingly receive the mandrel 32 therein. The entire pressure vessel assembly 50 may be held together via screws/bolts 71.

The upper diameter 40 of the mandrel 32 is about the same size as the diameter of the upper opening 54 of the pressure vessel 50. Similarly, the lower diameter 36 of the mandrel 32 is about the same size as the diameter of the lower opening 58 of the pressure vessel 50. With this sizing and configuration of the upper and lower mandrel portions 38, 34 largely matching the size and shape of the pressure vessel upper and lower openings 54, 58, the mandrel can be positioned within the pressure vessel central lumen 68 with a relatively tight fit between the upper and lower plates and the mandrel.

The shaping balloon 64 is formed from a membrane 70 having an upper edge 72 and a lower edge 74. The upper edge 72 is sandwiched between the upper plate 52 and the central plate 60, while the lower edge 74 is sandwiched between the central plate 60 and the lower plate 56. The shaping balloon 64 when viewed from above preferably has a generally ring-like or circular shape. Shaping balloons according to the invention may be in various shapes and configurations, including configuration where multiple balloon envelopes are assembled around a perimeter to form a shaping balloon assembly. Substantially circular shapes such as that depicted in FIGS. 2A-2E may be preferable for compressing stents. For stents having a relatively short length compared the width, such as those configured for support of heart valve leaflets in a prosthetic heart valve assembly, a shaping balloon may be formed in a toroidal shape. For example, in FIGS. 2A-2E, the shaping balloon 64 is formed substantially as the inner half of a toroid, and more specifically as the inner half of a toroid with substantially circular cross-section, i.e., a torus.

A fluid lumen 76 passes through the central plate and is in fluid communication within the interior chamber 78 of the shaping balloon 64. A pressure vessel 50 according to the invention may have a pressure gauge fluidly connected to the balloon interior chamber 78 (e.g., via the fluid lumen 76) for monitoring the pressure level therewithin. The balloon interior chamber may be pressurized with a fluid, and may preferably be a liquid for minimum compressibility. However, the balloon interior chamber may alternatively be pressurized with a gas. The pressurization of the balloon interior chamber may typically be facilitated by a balloon inflation device, such as that used for angioplasties (e.g., a syringe used to inflate the balloon) or other pressure sources, such as a compressed air line or hydraulic line. In some instances, the balloon inflation device may include its own pressure gauge. Alternatively, a separate pressure gauge may be fluidly connected to the balloon interior chamber. Note that alternative devices may be used to pressurize the balloon interior chamber.

The pressure vessel 50 is depicted by itself in FIG. 3. The balloon 64 is in its unexpanded configuration, wherein the balloon inner opening 66 has a diameter 80a which is equal to or less than the diameters of the upper and/or lower openings 54, 58, so that the balloon 64 will not obstruct the pressure vessel central lumen 68 and will not interfere with the movement of the mandrel into and out of the pressure vessel central lumen 68. Note that even in the so-called "unexpanded" configuration, the balloon 64 may have some fluid therein.

A mandrel of the invention can be formed into any desired shape. Mandrels 32a-32e according to embodiments of the invention may have various profiles, such as those profiles 44a-44e depicted in FIGS. 4A-4E, for their stent-support portions 42a-42e. FIG. 4A depicts a mandrel 32a having a substantially constant-diameter cylindrical profile 44a. FIG. 4B depicts a generally tapered mandrel 32b with a tapering profile 44b along the length of the stent-support portion 42b. In FIG. 4C, a mandrel 32c has a profile 44c which is wider toward the bottom, narrower in the middle, and wider again at the top of the stent-support portion 42c. In FIG. 4D, a mandrel 32d has a profile 44d which is narrower toward the bottom, wider toward the center, and then narrower at the top of the stent-support portion 42d. FIG. 4E depicts a mandrel 32e where the stent-support portion 42e starts wide at the bottom, narrows further up, widens again further up, and then narrows at the top. Note that mandrels of the invention may have detachable portions along their lengths to facilitate stent attachment and/or removal from the mandrel. For example, as depicted in FIG. 4C, the mandrel 32c has a separation line 82 at the narrowest point, where an upper mandrel half 84a can be separated from a lower mandrel half 84b to facilitate stent removal and/or attachment.

A stent 10 is initially positioned on a mandrel 32, with the stent 10 in a substantially simple constant-diameter cylindrical configuration (i.e., a pre-shaped configuration), as depicted in FIG. 5. Note that the stent 10 in this initial configuration has a maximum outer diameter 86 which is less than the upper diameter 40 and/or lower diameter 36, so that the stent 10 rests securely in the recessed stent-support portion and will not interfere with the mandrel 32 being slidingly advanced into the pressure vessel (as depicted in FIG. 6). This initial positioning of the stent onto the mandrel may include sliding the stent over the mandrel and partially crimping the stent to a slightly reduced profile so that its maximum outer diameter is less than the upper diameter 40 and/or lower diameter 36. For a mandrel with removable portions, initial positioning may include removing one or more of the removable portions to permit the stent to slide onto the stent-support portion with minimal, or no, initial crimping. For example, initial positioning of the stent 10 may include removing the mandrel upper portion 38, sliding the stent 10 over the mandrel central stent-support portion 42 from the top, and replacing the mandrel upper portion 38. As another example, initial positioning of the stent 10 may include removing the mandrel lower portion 34, sliding the stent 10 over the mandrel central stent-support portion 42 from the bottom, and replacing the mandrel lower portion 34.

In FIG. 6, the mandrel 32 is fully seated within the pressure vessel central lumen 68, with the stent 10 and stent-receiving portion 42 positioned longitudinally adjacent the shaping balloon 64, the mandrel upper portion 38 adjacent the upper plate 52, and the mandrel lower portion 34 adjacent the lower plate 56. The shaping balloon 64 is in its unexpanded configuration.

Fluid is introduced into the balloon interior chamber 78 via the fluid lumen 76 to expand the shaping balloon 64 to its expanded configuration. The pressure exerted by the shaping balloon 64 compresses the stent 10 against the mandrel 32 to give the stent 10 its desired shape, as depicted in FIG. 7. The fluid is provided at a pressure sufficient to compress the stent 10 to the desired shape. The pressure required for stent compressions/shaping will vary according to the particular application, including specifics such as the radial strength of the pre-shaped stent, etc. For example, a stent with more rigid characteristics may require higher fluid pressures for the balloon to compress the stent to the desired shape. Pressures for use with the invention may be in the range of about 75 to 150 psi, depending on the particular application. Other pressures are also within the scope of the invention.

After the stent 10 is compressed to the desired shape, the balloon 64 can be deflated to its unexpanded configuration, and the mandrel 32 with shaped stent 10 thereon can be slid out of the pressure vessel 50. To facilitate stent removal, the mandrel may include one or more detachable/re-attachable portions. For example, as depicted in FIGS. 8A and 8B, the upper portion 38 of the mandrel 32 may be detachable and/or re-attachable from the stent-support portion 42. With the upper portion 38 removed, as shown in FIG. 8B, the shaped stent 10 can be easily slid off the top of the mandrel 32.

Note that the lower portion of the mandrel may similarly be detachable and/or re-attachable from the stent support portion. Additionally, the mandrel stent-support portion 42 may itself have portions which are detachable and/or re-attachable.

As depicted in FIG. 9, the mandrel 32 may include a rigid inner portion 86 with a coating 88 of a resilient material on the central stent-support portion 42 which can be partially compressed. The resilient coating 88 may provide some padding for a stent as it is compressed into the mandrel 32. The resilient coating 88 may make it possible for a prosthetic heart valve assembly to be compressed onto the mandrel in its assembled form (e.g., with valve leaflets secured to the stent interior), with the resilient coating 88 providing a cushion to protect the valve leaflets as the stent is compressed onto the mandrel to assume the desired shape.

A mandrel 32 of the invention may include one or more heating elements 90, which may be used to apply heat to the mandrel 32 in order to set the shape of a shape-memory stent being compressed, either alone or as a partially- or completely-assembled medical device (e.g., assembled heart valve) into the form of the mandrel 32.

FIGS. 10A-10B depict a pressure vessel 50 with shaping balloon 64, wherein the shaping balloon 64 is formed from a flexible but substantially inelastic material, and may include substantially non-elastic cords and/or be formed from specific shape-enhancing materials (e.g., Kevlar, etc.) to further refine the shape. In FIG. 10A, the balloon 64 is substantially deflated and is radially retracted with respect to the pressure vessel central lumen 68. In the deflated condition, the balloon 64 may have folds 92. In FIG. 10B, the balloon 64 is expanded, and forms a pre-determined shape even without the presence of a mandrel. Such a predetermined balloon shape may cooperate with the shape of the mandrel to provide even pressure and/or compression across a stent as it is compressed between the balloon and mandrel. Note that the choice of elastic v. non-elastic balloon materials depends on the particular application.

The shaping balloon of the present apparatus may be fabricated from various materials, including elastomeric and/or non-elastomeric materials, depending on the particular application. For example, polyethylene (PE), polyethylene terephthalate (PET), and nylon may be used for balloons. If the device is to be used to shape-set memory materials such as nitinol, the balloon may preferably be formed of materials resistant to the temperatures involved. Materials like Ethylene Propylene Diene Rubber (EPDM), TFE/Propropylene Rubber (FEPM), Silicone Rubber (VMQ) and Perfluorinated Elastomer (FFKM) may be options for balloon materials. For example, if heat is to be provided, e.g., from the mandrel or via the balloon itself (such as via hot fluid being provided therein), the balloon material may preferably be resistant to being damaged or otherwise compromised by the heat being provided. Alternatively, relatively cool fluid may be pumped into the balloon interior to cool the balloon and prevent the balloon material from being damaged by the shape-set memory temperatures to which the stent is being exposed.

Stents for use with the invention may be formed of various biocompatible materials. For a shape-memory material stent, the method may be varied to achieve shape setting when the stent is in the compressed configuration (i.e., with the shaping balloon expanded and compressing the stent onto the mandrel). For example, after or during the step of inflating the shaping balloon with sufficient pressure to cause the shaping balloon to expand to its expanded configuration, and while the stent is compressed against the mandrel (and prior to deflating the shaping balloon) it may be desirable to expose the stent to a desired shape-setting temperature, and then to reduce the temperature to end the shape-setting process. Exposing the stent to the desired temperature may include applying heat via heating elements, such as those depicted in FIG. 10 as elements 90, and reducing the temperature after setting the shape may include discontinuing power to the heating element(s). Exposing the stent to the desired shape-setting temperature may include introducing heated fluid into the interior chamber of the shaping balloon, with the heating fluid being provided at a temperature that is at or above the desired shape-setting temperature. Exposing the stent to the desired reduced temperature may involve adding to the balloon interior chamber fluid having a temperature that is at or below the desired shape-setting temperature.

While the invention has been described in its preferred embodiments, it is to be understood that the words which have been used are words of description and not of limitation. Therefore, changes may be made within the appended claims without departing from the true scope of the invention.

What is claimed is:

1. An apparatus for shaping stents, comprising:
a pressure vessel comprising:
an upper plate comprising an upper plate opening passing through the upper plate;
a lower plate comprising a lower plate opening passing through the lower plate;
a central plate assembly comprising a central plate and central plate opening defining an inner perimeter, the central plate assembly further comprising an annular shaping balloon, the shaping balloon having a balloon opening and defining a balloon interior chamber, the shaping balloon passing around the inner perimeter of the central plate opening, the shaping balloon having an inflated configuration and a deflated configuration, the central plate assembly further comprising a fluid lumen in fluid communication with the balloon interior chamber;
wherein the upper plate and lower plate and central plate are stacked together with the central plate positioned between the upper plate and the lower plate, and wherein the lower plate opening, upper plate opening, and balloon opening form a continuous mandrel-receiving lumen; and
a mandrel comprising a mandrel longitudinal axis, the mandrel comprising an upper mandrel portion, a lower mandrel portion, and a central mandrel portion defining a stent-receiving area, wherein the upper mandrel portion comprises a shape configured to fit tightly into the upper plate opening, the lower mandrel portion comprises a shape configured to fit tightly into the lower plate opening, and the central mandrel portion comprises a shape corresponding to a desired stent shape, wherein the mandrel is sized and configured to be slidingly advanced along its longitudinal axis into the mandrel-receiving lumen with a stent positioned around the stent-receiving area so that inflation of the annular shaping balloon compresses the stent radially inward against the stent-receiving area.

2. The apparatus of claim 1, wherein the upper mandrel portion comprises an upper diameter, the lower mandrel portion comprises a lower diameter, and the stent-receiving area comprising one or more areas of reduced radial diameter, wherein the one or more areas of reduced radial diameter are smaller in diameter than at least one of the upper diameter or lower diameter.

3. The apparatus of claim 2, wherein the one or more areas of reduced radial diameter are smaller in diameter than both the upper diameter and lower diameter.

4. The apparatus of claim 3, wherein the upper diameter and the lower diameter are equal.

5. The apparatus of claim 2, wherein the stent-receiving area comprises a substantially tubular shape having varying diameters along a longitudinal length thereof.

6. The apparatus of claim 2, wherein the stent-receiving area comprises a substantially tubular shape having a substantially constant diameter along a longitudinal length thereof.

7. The apparatus of claim 2, wherein the upper mandrel portion is configured to be releasably attached and re-attached to the central mandrel portion.

8. The apparatus of claim 2, wherein the lower mandrel portion is configured to be releasably attached and re-attached to the central mandrel portion.

9. The apparatus of claim 1, wherein the stent-receiving portion of the mandrel comprises an outer surface which is formed from substantially flexible material.

10. The apparatus of claim 1, wherein the mandrel comprises an inner shape which is formed from substantially rigid, non-deformable material.

11. The apparatus of claim 1, wherein the shaping balloon comprises an upper edge and a lower edge, wherein the upper edge of the shaping balloon is sandwiched between an upper surface of the central plate and a lower surface of the upper plate, wherein the lower edge of the shaping balloon is sandwiched between a lower surface of the central plate and an upper surface of the lower plate.

12. The apparatus of claim 1, wherein the shaping balloon is formed of substantially elastomeric material.

13. The apparatus of claim 1, wherein the shaping balloon is formed from substantially flexible but substantially non-elastomeric material.

14. The apparatus of claim 1, further including a heating element mounted in the mandrel adjacent the stent-receiving portion thereof.

15. An apparatus for shaping stents, comprising:
a pressure vessel defining a central opening having upper and lower walls and an inner perimeter wall therebetween, a continuous lumen extending through the pressure vessel defined by upper and lower openings in the upper and lower walls, respectively;
an annular shaping balloon sized to fit between the upper and lower walls and against the inner perimeter wall of the central opening and having an inner balloon opening, the shaping balloon having an inflated configuration and a deflated configuration, wherein in the deflated configuration of the shaping balloon the inner balloon opening has a greater diameter than both the upper and lower openings so as not to extend into the continuous lumen, the pressure vessel further comprising a fluid lumen in fluid communication with an interior chamber of the shaping balloon; and
a mandrel defining a mandrel longitudinal axis and comprising an upper mandrel portion with a shape configured to fit tightly into the upper opening, a lower mandrel portion with a shape configured to fit tightly into the lower opening, and a central mandrel portion defining a stent-receiving area comprising one or more areas of reduced radial diameter that are smaller in radial dimension than both the upper and lower mandrel portions, and the stent-receiving area comprises a shape corresponding to a desired stent shape, wherein the mandrel is sized and configured to be slidingly advanced along its longitudinal axis into the lumen with a stent positioned around the stent-receiving area so that inflation of the annular shaping balloon compresses the stent radially inward against the stent-receiving area.

16. The apparatus of claim 15, further including a heating element mounted in the mandrel adjacent the stent-receiving portion thereof.

17. The apparatus of claim 15, wherein the stent-receiving area comprises a substantially tubular shape having varying diameters along a longitudinal length thereof.

18. The apparatus of claim 15, wherein at least one of the upper or lower mandrel portions is configured to be releasably attached and re-attached to the central mandrel portion.

19. The apparatus of claim 15, wherein the stent-receiving portion of the mandrel comprises an outer surface which is formed from substantially flexible material.

20. The apparatus of claim 15, wherein the mandrel comprises an inner shape which is formed from substantially rigid, non-deformable material.

21. The apparatus of claim 15, wherein the shaping balloon is formed of substantially elastomeric material.

22. The apparatus of claim 15, wherein the shaping balloon is formed from substantially flexible but substantially non-elastomeric material.

* * * * *